United States Patent
Guy

(10) Patent No.: US 8,650,970 B2
(45) Date of Patent: Feb. 18, 2014

(54) TEST RIG FOR TESTING BLADES FOR A WIND TURBINE

(75) Inventor: Stuart Guy, Lockerley (GB)

(73) Assignee: Vestas Wind Systems A/S, Aarhus N. (DK)

( * ) Notice: Subject to any disclaimer, the term of this patent is extended or adjusted under 35 U.S.C. 154(b) by 320 days.

(21) Appl. No.: 13/001,801

(22) PCT Filed: Jun. 30, 2009

(86) PCT No.: PCT/EP2009/058141
§ 371 (c)(1), (2), (4) Date: Mar. 25, 2011

(87) PCT Pub. No.: WO2010/000711
PCT Pub. Date: Jan. 7, 2010

(65) Prior Publication Data
US 2011/0179884 A1    Jul. 28, 2011

Related U.S. Application Data

(60) Provisional application No. 61/133,694, filed on Jun. 30, 2008.

(30) Foreign Application Priority Data

Jun. 30, 2008 (DK) .......................... PA 2008 00906

(51) Int. Cl.
*G01L 1/00* (2006.01)

(52) U.S. Cl.
USPC ........................................ 73/862.381; 73/168

(58) Field of Classification Search
USPC ..................... 73/168, 760, 862.381
See application file for complete search history.

(56) References Cited

U.S. PATENT DOCUMENTS

| | | | | |
|---|---|---|---|---|
| 4,381,902 A | * | 5/1983 | Head et al. | 416/134 A |
| 4,776,216 A | * | 10/1988 | Barton et al. | 73/660 |
| 4,924,706 A | * | 5/1990 | Moore | 73/579 |
| 6,814,543 B2 | * | 11/2004 | Barb et al. | 416/1 |
| 2006/0037402 A1 | | 2/2006 | Musial et al. | |
| 2010/0263448 A1 | * | 10/2010 | Hughes et al. | 73/577 |
| 2010/0275695 A1 | * | 11/2010 | Cotrell et al. | 73/663 |

FOREIGN PATENT DOCUMENTS

| | | |
|---|---|---|
| JP | 4-164231 | 6/1992 |
| WO | 2008/145727 | 12/2008 |
| WO | 2009/097055 | 8/2009 |

OTHER PUBLICATIONS

Lars Kolby; International Search Report and Written Opinion issued in priority application No. PCT/EP2009/058141; Sep. 3, 2010; 18 pages; European Patent Office.

* cited by examiner

*Primary Examiner* — Max Noor
(74) *Attorney, Agent, or Firm* — Wood, Herron & Evans, LLP

(57) ABSTRACT

A test rig for testing blades for a wind turbine includes a fixing structure where a root end of a wind turbine blade can be fixed, a loading mass structure extending from the fixing structure, and an actuation structure which can apply a sinusoidal force to the loading mass structure so that a counterbalanced resonance is established between the loading mass structure and a blade which is fixed in the fixing structure. Due to the counterbalanced resonance, the force from the test rig onto the floor or other building components can be reduced relative to that known from the traditional rigs for blade testing.

22 Claims, 1 Drawing Sheet

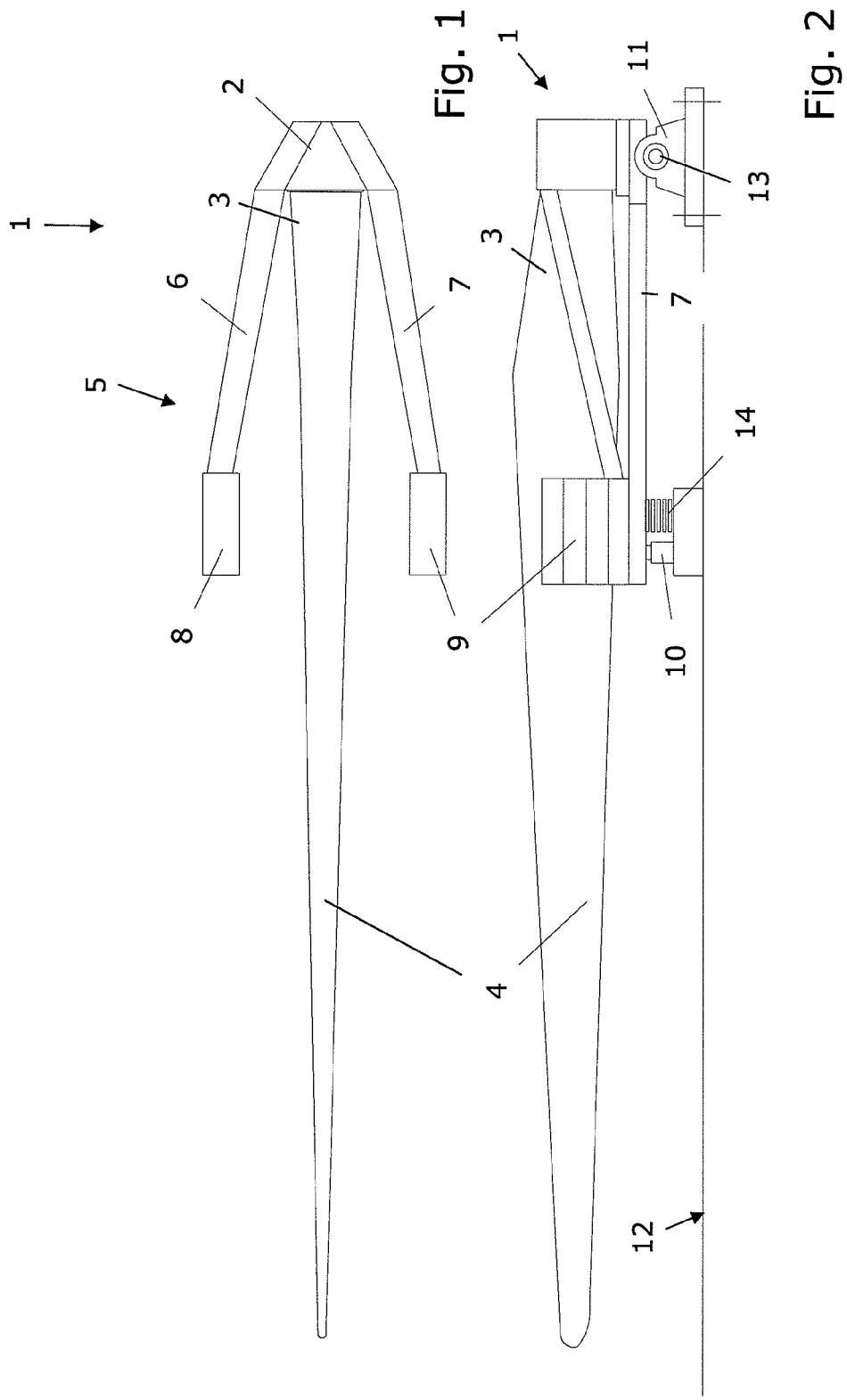

TEST RIG FOR TESTING BLADES FOR A WIND TURBINE

The invention relates to a test rig for testing blades for a wind turbine. The test rig comprises a fixing structure in which a blade for a wind turbine can be fixed and an actuation structure which is arranged to excite the blade and cause an oscillating movement and bending of the blade.

BACKGROUND

Wind turbines for producing electricity typically use slender turbine blades extending radially from a hub. The hub is mounted to a shaft which drives a generator. Wind turbines are made larger and larger, and the static and dynamic loads on the turbine blades therefore increase.

In blade testing, static loads may be useful for evaluating stiffness and ultimate strength of a turbine blade. However, in practice, the load on a wind turbine blade varies constantly and to evaluate fatigue resistance of the blade, a cyclical load may be applied in large test facilities.

During a typical test, a heavy load rotates eccentrically. The load is strapped to the blade at a location between the hub end and the tip end of the blade and therefore makes the blade oscillate.

Unfortunately, the rotating mass and the oscillating blade requires very large heavy duty building facilities due to the very large forces which are transferred into the floor and other building components during the oscillating movement of the very heavy components.

The wind turbine industry requires a cost effective and convenient method to test large wind turbine blade in fatigue to improve reliability in design and manufacture.

As the size of wind turbine blades increases, the fatigue test rigs require foundations that are expensive and time consuming to construct. In addition, wind turbine blades are now manufactured in many locations around the world and transportable test rigs capable of testing blades where they are manufactured are requested in an attempt to reduce transport costs and save time It is also desirable to reduce the impact of the test equipment on its ambient environment, for example, load on the building in which the test equipment operates, etc.

DESCRIPTION OF THE INVENTION

It is an object of the invention to provide a more flexible, lighter, or more easily movable test rig for testing large blades for wind turbines. It is a further object to facilitate blade testing with reduced requirements to strength and durability of the building complex of the test facility.

According to a first aspect, the invention provides a test rig for testing blades for a wind turbine, the test rig comprising a fixing structure where a root end of a wind turbine blade can be fixed, a loading mass structure extending from the fixing structure, and an actuation structure which can apply a force to the loading mass structure so that a counterbalanced resonance is established, for example, between the loading mass and a blade which is fixed in the fixing structure or between the loading mass and an additional loading mass.

Since the force is applied to establish a counterbalanced resonance between the loading mass and the blade, the rig does not transmit the same reaction forces into the ground or other building components, and the test rig can therefore be used within a wider range of building and testing facilities, and possible damage of the building, for example, the floor, may be reduced.

The blades may in general be any kind of blade for a wind turbine, and typically such blades are provided with a flange by which the blade is connected to the hub of the wind turbine. The fixing structure should transfer an oscillating movement of the loading mass to the blade, and the blade should therefore be fixed relatively solid to the fixing structure.

The blade could be fixed to the fixing structure by any kind of fixation means. As an example, the blade could be bolted onto the fixing structure. In fact, the fixing structure may partly be constituted by an element with the shape, or which at least functionally works like the hub of that wind turbine for which the blade is designed. Accordingly, the fixing structure may comprise a ring-shaped fixing flange with a number of through holes. To attach the blade, a matching ring-shaped end flange of the blade could be arranged against the fixing flange, and the blade could be bolted by bolts extending through the holes in the ring-shaped fixing flange into internal threadings in the root end of the wind turbine blade. In this way, not only the blade but also the interface between the blade and the hub can be tested.

The actuation structure comprises an actuating part which could be electrically, hydraulically or pneumatically driven, and it could include a rotating member with an eccentrically attached mass or lever arm. To avoid an excessive load and possible damage of the rig, the actuation structure is preferably in constant contact with the loading mass structure. As an example, the actuating part of the actuation structure comprises a movable part which moves relative to a fixed part. The movable part could be bolted, strapped or otherwise fastened to the loading mass while the fixed part is bolted or otherwise fastened to the ground below the rig or to other fixed building components. The actuating part may comprise a regular actuator, for example, in the form of a hydraulically driven or electrically driven piston moving in a cylinder.

The actuation structure is arranged to excite movement of the loading mass structure by contact with the loading mass structure at an excitation point thereof. The actuation structure may, for example, be movable relative to the loading mass structure so that the excitation point can be selected along the loading mass structure.

To hold the natural frequency of the loading mass as high as possible, it may be an advantage to design the actuation structure so that it does not increase the weight of the loading mass structure, for example, by having the weight of the actuation structure carried entirely by the building in which the rig operates, e.g. carried by the floor. Similarly, the blade should preferably not be weighed down by any elements attached thereto.

The actuation structure may further comprise an actuation control system which selects an excitation frequency for the system. The excitation frequency may, for example, be selected to provide a minimal input force relative to the amplitude of the achieved oscillation of the blade. The most efficient excitation frequency would normally be at, or near a natural frequency of the loading mass and/or the blade.

The frequency could be modulated by a digital sine wave generator controlled by a PC.

The input force could be determined in several different ways. One way is by arranging a strain sensitive structure, for example, a strain gauge, a fiber optic or similar means between the actuating part and the loading mass or at different locations on the actuating part and/or on the loading mass and/or on the blade which is tested. When the blade is deflected, the strain sensitive structure provides a signal representing the force by which the actuating part influences the blade. Another way is to measure the amount of energy which is consumed by the actuating part during deflection of the blade. Yet another way is to measure deflection of a link between the loading mass and the actuating part.

The signal from the strain sensitive structure or similar signal representing the force which is necessary to make the blade deflect can be sampled in a period of time in which the frequency is modulated. By relating the frequencies to the sampled input forces, it can be determined at which frequency least input force is necessary.

The force applied to the loading mass could particularly be a sinusoidal force. By sinusoidal force is herein meant a broader definition of the amplitude of the force having a succession of waves or curves, i.e., the force is varied to obtain oscillating movement of the loading mass and blade in counterbalanced resonance. The amplitude of the force may follow an exact mathematic sine shape, but it does not necessarily have to follow such a mathematic exact sine shape.

By counterbalanced resonance is herein meant that the loading mass structure and the blade moves with the same frequency in different directions, e.g. in opposite directions, e.g., the blade and the loading mass structure move either towards each other or away from each other.

To facilitate the counterbalanced resonance, the loading mass structure may be arranged on, or form part of one or more elongated loading arms extending from the fixing structure or at least from a place in the vicinity of the fixing structure. The loading mass structure is connected to the fixing structure so that oscillating movement of the loading mass structure is transferred to the fixing structure and therefrom further to the blade which is tested.

In particular, the loading mass structure may be constituted by two loading arms which extend from the fixing structure on opposite sides of the blade. The two loading arms may in particular be identical arms with identical geometry and/or weight. In one embodiment, the loading arms are detachably attached to the fixing structure so that a loading arm can be replaced with another arm, for example, for changing geometry or weight of the arm.

The actuation structure may comprise at least one actuator for each loading arm.

To enable testing of blades having different geometry or weight, and therefore different natural frequency, the rig may include adjustment means by which the mass of the loading mass structure can be changed, or by which the length by which the loading mass structure extends away from the fixing structure can be changed.

The previously mentioned loading arms may, for example, have a variable length, or each arm may comprise a reaction mass which is either movable relative to the arm or which is detachable and therefore allows replacement with a reaction mass with a different weight. In one embodiment, one or more elements, for example, of different weight can be attached along an arm of a fixed or variable length. In that way, the natural frequency of the loading arm may be adjusted by selection of a specific distance from the fixing structure to the element or elements.

In that way, a distance from the reaction mass to either the excitation point or to the fixing structure can be varied or the mass of the loading mass structure can be changed.

To enable variations in the resonance frequency of the blade, the blade may further be confined or fixed at different locations along the blade. As an example, the testing may be interesting particularly with respect to a tip end of the blade. By fixing the blade to the floor or any other surrounding obstacle at a location between the hub end and tip end of the blade, the tip end of the blade may oscillate faster, and the duration of the test can be decreased further. Accordingly, the rig may comprise at least one fixation means which is adjustable to allow fixation of the blade to a surrounding object at different locations along the blade.

The rig may comprise an additional actuator adapted to deflect the blade at an excitation frequency which could be equal to the frequency of the previously mentioned actuating part or which could be different from the excitation frequency of the previously mentioned actuating part. The additional actuator could be adjustably positioned along the blade to cause deflection at different points along the blade.

In fact, to enable variations in the resonance frequency of the blade, the rig may comprise any number of fixtures for fixing the blade to a surrounding object, e.g. to the floor of the test area, and any number of actuators arranged to deflect the blade at different locations along the blade.

The rig may comprise a base which supports placement of the test rig on a ground and which allows rotational movement of the fixing structure and the loading mass structure around a hinge point relative to the base.

The fixing structure may be adapted for fixing a blade so that it extends unsupported from the fixing structure in its full length. For this purpose, the rig may comprise an anchoring structure, which anchors the rig to a floor or wall of a building in which the rig is placed. Via the anchoring structure, the moment of inertia from the blade on the rig can be transferred into a fixed building component.

The rig may further comprise a damping structure arranged to dampen movement of the loading mass structure and/or to dampen movement of a blade which is tested. The damping structure may comprise a body of an elastically deformable material, e.g. rubber material, which is arranged between a fixed building component and the loading mass structure.

In a second aspect, the invention provides a method of testing a blade for a wind turbine, the method comprising fixing the blade to the fixing structure of a rig of the kind according to the first aspect of the invention. The blade is moved and deflected by applying a sinusoidal force to the loading mass structure, the force being applied so that a counterbalanced resonance is established between the loading mass structure and the blade.

The method may in particular comprise the step or steps of repeatedly modulating the frequency and subsequently re-selecting the excitation frequency during a test. This is in order to take changes to the natural frequency of a blade into consideration, and for tests with a long duration, this may be important for the test result as well as the economy of the test.

In a third aspect, the invention provides a control system for controlling a rig of the kind described relative to the first aspect of the invention. The control system being adapted to modulate an excitation frequency at which the actuation structure applies a force to the loading mass structure, to determine an input power consumed by the actuation structure to apply the force to the loading mass structure, to determine an amplitude of movement of the blade or loading mass structure, and to select an excitation frequency based on a ratio between the input force and the amplitude. The invention may be implemented in a software product for execution on a regular PC via a standard interface to a servo-amplifier or by similar interface to the actuator.

The rig and method may in fact be applied for testing blades not only for wind turbines but also for testing propeller blades for ventilators, ships, helicopters etc.

DETAILED DESCRIPTION

In the following, embodiments of the invention will be described in further details with reference to the drawings in which:

FIG. 1 illustrates a test rig according to the invention in a top view; and

FIG. 2 illustrates the test rig from FIG. 1 in a side view.

The test rig 1 is suitable for testing blades for a wind turbine, but could also be used for testing similar elongated components of a large size, e.g. up to 50 meters length of more. The test rig 1 comprises a fixing structure 2 where a root end 3 of a wind turbine blade 4 can be fixed. The rig comprises a loading mass structure 5 with arms 6, 7 which extend from the fixing structure 2 on opposite sides of the blade 4. The arms 6, 7 extend between the fixing structure 2 and reaction masses 8, 9. The reaction masses are provided so that the weight of each mass can be varied individually by adding additional weight elements or by removing weight elements from each arm. Additionally, the reaction masses can be located at various locations along the arms.

The rig further comprises an actuation structure with actuators 10 arranged below each of the loading mass structures. The actuators are controllable for application of a sinusoidal force to the loading mass structure so that a counterbalanced resonance is established between the loading mass structures and the blade 4.

The test rig further comprises a base 11 which supports placement of the test rig on a horizontal ground 12. The fixing structure 2 and the loading mass structure 5 are rotationally hinged to the base so that they can rotate about the pin 13.

As illustrated, the fixing structure is sufficiently strong, and the rig is anchored to the ground which enables the blade can extend unsupported from the fixing structure in its full length.

The damping structure 14 is provided below each arm and dampens the oscillating movement thereof.

The rig further comprises a control system which is not illustrated in FIG. 1 but which in the following is described in further details:

The control system may comprise a set of strain sensitive structures which can be fixed to the blade or the loading mass structure at different locations. The strain sensitive structures can be used for determining a deflection, e.g. for determining the amplitude of the deflection, or the strain sensitive structures can be used for determining a general condition of the blade, e.g. to observe changes in the blade throughout the fatigue testing. The signals from the strain sensitive structures are collected and used in a frequency modulation algorithm.

The control system further comprises a frequency modulation structure which can perform the following steps:

An approximation of the natural frequency is selected manually in the first instance.

The control system continuously modulates the frequency by a small amount above and below the selected frequency.

The control system monitors the amplitude from the strain sensitive structures and compares this with the mean force input and calculates the efficiency.

The selected frequency is then reset to the value that gives the highest efficiency. In this way, the frequency of operation moves toward the most efficient operating condition automatically for varying conditions.

A separate control loop running concurrently ensures the amplitude of the strain is maintained at the level required for the test.

The frequency algorithm delivers control signals for amplitude and frequency modulation control. The control signal could be in the form of voltages proportional to amplitude and frequency as inputs to the digital sine wave generator.

The signal is received e.g. by a digital signal generator which in response generates a signal to control the actuator, e.g. an on/off signal or a proportional signal for a valve which controls a flow of a fluid under pressure to a hydraulic actuator.

The invention claimed is:

1. A test rig for testing blades for a wind turbine, the test rig comprising a fixing structure where a root end of a wind turbine blade can be fixed, a loading mass structure extending from the fixing structure, and an actuation structure which can apply a force to the loading mass structure so that a counterbalanced resonance is established.

2. The test rig according to claim 1, wherein the loading mass structure comprises at least one loading arm extending from the fixing structure, each loading arm comprising a reaction mass being movable relative to the fixing structure.

3. The test rig according to claim 2, wherein the loading arms extend from opposite sides of a fixing point from which a blade, which is fixed in the fixing structure, extends.

4. The test rig according to claim 2, wherein the actuation structure comprises at least one actuator for each loading arm.

5. The test rig according to claim 1, wherein the actuation structure is movable relative to the loading mass structure so that an excitation point at which the actuation structure contacts the loading mass structure can be selected at different locations on the loading mass structure.

6. The test rig according to claim 1, further comprising a base which supports placement of the test rig on a ground, wherein the fixing structure and loading mass structure are rotationally hinged to the base.

7. The test rig according to claim 1, wherein the fixing structure is adapted for fixing a blade so that it may extend unsupported from the fixing structure in its full length.

8. The test rig according to claim 7, comprising an anchoring structure by which the rig may be anchored to a fixed building component.

9. The test rig according to claim 1, further comprising a damping structure arranged to dampen movement of the loading mass structure.

10. The test rig according to claim 1, wherein the actuation structure comprises an actuation control system which can select an excitation frequency for the system.

11. The test rig according to claim 10, wherein the control system can analyze oscillation of the loading mass structure or a blade which is fixed in the fixing structure, and based thereon, select an excitation frequency which provides a minimal input force relative to the amplitude of the achieved oscillation of the blade or loading mass structure.

12. The test rig according to claim 1, wherein the force applied to the loading mass is a sinusoidal force.

13. The test rig according to claim 1, wherein the counterbalanced resonance is established between the loading mass structure and a blade which is fixed in the fixing structure.

14. A method of testing a blade for a wind turbine, the method comprising:

providing a test rig including a fixing structure where a root end of a wind turbine blade can be fixed, a loading mass structure extending from the fixing structure, and an actuation structure which can apply a force to the loading mass structure so that a counterbalanced resonance is established, fixing the blade to the fixing structure of the test rig, and exciting an oscillating movement on the blade by applying a sinusoidal force to the loading mass structure, the force being applied so that a counterbalanced resonance is established between the loading mass structure and the blade.

15. The method according to claim 14, wherein the movement is excited at an excitation frequency and input force, at least one of which is modulated during the test.

16. A control system for controlling a rig according claim 1, the control system being adapted to modulate an excitation frequency at which the actuation structure applies a force to the loading mass structure, to determine an input power consumed by the actuation structure when applying force to the loading mass structure, to determine an amplitude of movement of the blade or loading mass structure, and to select an excitation frequency based on a ratio between the input force and the amplitude.

17. The method according to claim 14, further comprising:
providing a control system for controlling the test rig, wherein using the control system, the method further comprises:
modulating an excitation frequency at which the actuation structure applies a force to the loading mass structure,
determining an input power consumed by the actuation structure when applying force to the loading mass structure,
determining to determine an amplitude of movement of the blade or loading mass structure, and
selecting an excitation frequency based on a ratio between the input force and the amplitude.

18. A test rig for testing blades for a wind turbine, comprising:
a fixing structure coupled to a fixed building component such that forces acting on the fixing structure are transferred to the fixed building component, wherein the fixing structure is configured to fixedly receive a root end of a wind turbine blade;
a loading mass structure extending from the fixing structure by an arm such that the fixing structure supports the loading mass structure; and
an actuation structure coupled to the loading mass structure for applying a force thereto,
wherein when a wind turbine blade is coupled to the test rig and the actuation structure activated, the wind turbine blade vibrates such that a first reaction force is established at the fixing structure through the blade, and the loading mass structure moves such that a second reaction force is established at the fixing structure through the arm, the first and second reaction forces establishing a counterbalanced resonance between the loading mass structure and the blade such that the net force transferred to the fixed building component is reduced as compared to the first reaction force.

19. The test rig according to claim 18, wherein the loading mass structure is configured to be spaced from the wind turbine blade and coupled to the blade only through the fixing structure.

20. The test rig according to claim 18, wherein the actuation structure is coupled to a fixed building component.

21. A test rig for testing blades for a wind turbine, the test rig comprising a fixing structure where a root end of a wind turbine blade can be fixed, a loading mass structure extending from the fixing structure, and an actuation structure which can apply a force to the loading mass structure so that a counterbalanced resonance is established, wherein the loading mass structure comprises at least one loading arm extending from the fixing structure, each loading arm comprising a reaction mass being movable relative to the fixing structure.

22. A test rig for testing blades for a wind turbine, the test rig comprising a fixing structure where a root end of a wind turbine blade can be fixed, a loading mass structure extending from the fixing structure, and an actuation structure which can apply a force to the loading mass structure so that a counterbalanced resonance is established, wherein the actuation structure is movable relative to the loading mass structure so that an excitation point at which the actuation structure contacts the loading mass structure can be selected at different locations on the loading mass structure.

* * * * *

UNITED STATES PATENT AND TRADEMARK OFFICE
CERTIFICATE OF CORRECTION

PATENT NO. : 8,650,970 B2
APPLICATION NO. : 13/001801
DATED : February 18, 2014
INVENTOR(S) : Stuart Guy It is certified that error appears in the above-identified patent and that said Letters Patent is hereby corrected as shown below:

In the Claims

CLAIM 16
Column 7, lines 4-5, "according claim 1" should be -- according to claim 1 --

CLAIM 17
Column 7, line 22, "determining to determine" should be -- determining --

Signed and Sealed this
Twenty-first Day of October, 2014

Michelle K. Lee
*Deputy Director of the United States Patent and Trademark Office*